US008603393B1

(12) United States Patent
DolceAmore

(10) Patent No.: US 8,603,393 B1
(45) Date of Patent: Dec. 10, 2013

(54) ORAL SANITARY SYSTEM FOR SPORTS

(76) Inventor: Albert Charles DolceAmore, Allentown, PA (US)

( * ) Notice: Subject to any disclaimer, the term of this patent is extended or adjusted under 35 U.S.C. 154(b) by 511 days.

(21) Appl. No.: 12/958,375

(22) Filed: Dec. 1, 2010

Related U.S. Application Data

(60) Provisional application No. 61/265,750, filed on Dec. 1, 2009.

(51) Int. Cl.
*A61L 2/18* (2006.01)
(52) U.S. Cl.
USPC .......................................................... 422/28
(58) Field of Classification Search
USPC .............................................. 422/28; 134/34
See application file for complete search history.

(56) References Cited

FOREIGN PATENT DOCUMENTS

| JP | 2010-180361 A | * | 8/2010 |
| WO | WO 87/05779 | * | 10/1987 |

OTHER PUBLICATIONS

English language machine translation of JP 2010-180361 A, published: Aug. 19, 2010, inventor: Takahashi et al.*

* cited by examiner

*Primary Examiner* — Sean E Conley
(74) *Attorney, Agent, or Firm* — McNeely, Hare & War LLP; William D. Hare

(57) ABSTRACT

The invention generally relates to a mouthguard system that includes a mouthguard portion and a tether portion. The mouthguard portion is configured to be placed around a portion of a wearer's teeth and having an elongated member extending from the mouthguard portion, the elongated member including a magnet. The tether portion has a first end and a second end, the first end including a magnetic configured to mate with the magnet in the elongated member. The invention also relates to a method of cleansing or sanitizing an object to be placed in the mouth. The method includes spraying a solution of chlorhexidine gluconate on the object in an amount sufficient to cleanse or sanitize the object. The solution includes an aqueous carrier and chlorhexidine gluconate present at a concentration in the solution of about 0.02% to about 1.2%.

16 Claims, 2 Drawing Sheets

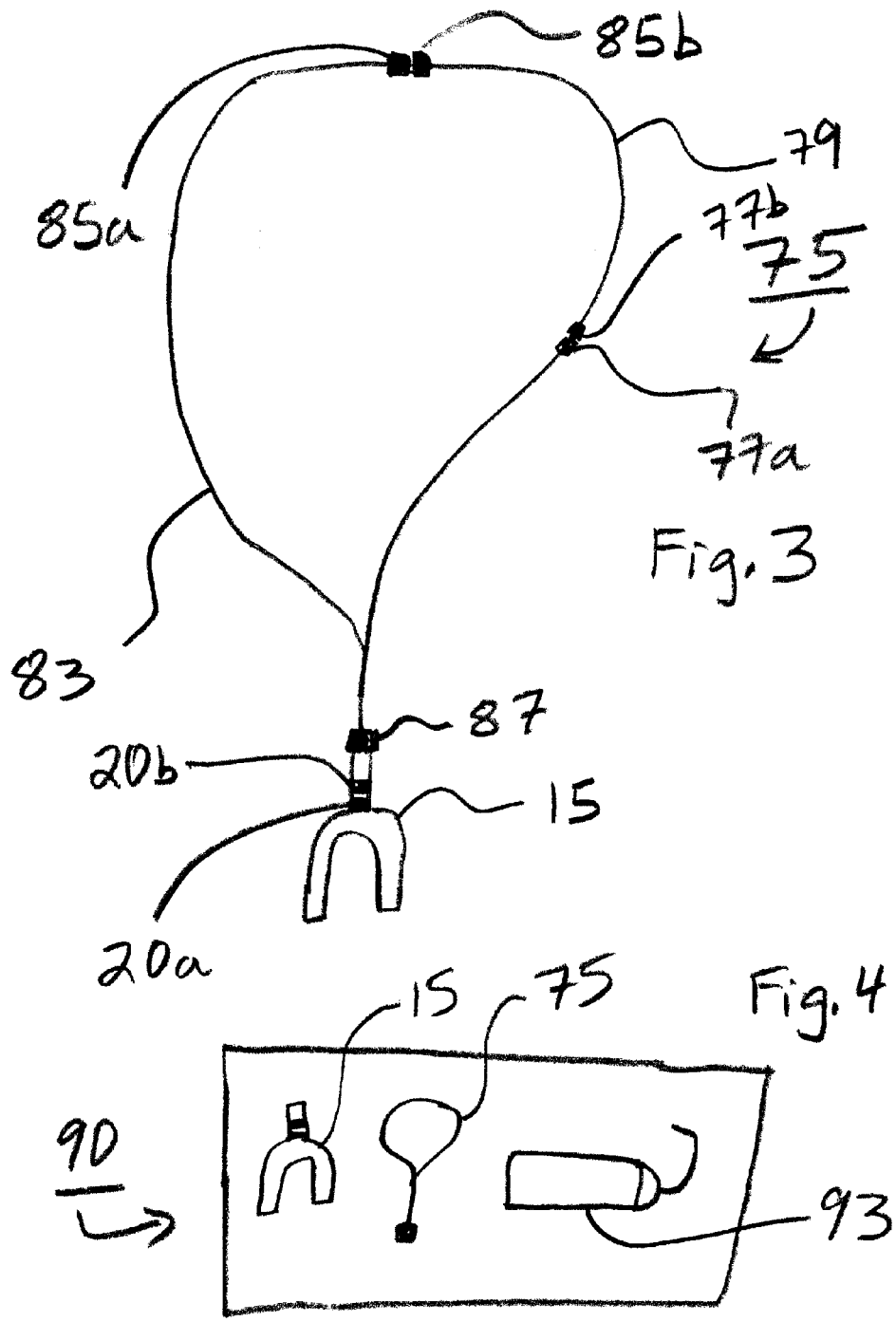

ORAL SANITARY SYSTEM FOR SPORTS

CROSS-REFERENCE TO RELATED APPLICATIONS

This application claims priority from provisional patent application No. 61/265,750 filed on Dec. 1, 2010, the contents of which are incorporated herein in their entirety by reference.

TECHNICAL FIELD

The field of the invention generally relates to a mouthguard with a detachable tether or strap for sports participants to use in athletic events and a cleaning/sanitizing solution for cleaning or sanitizing the mouthguard. The mouth guard can be provided alone or as a part of a system with the cleaning/sanitizing fluid to remove undesirable fluids and contaminants from the mouthguard during play.

BACKGROUND

Individuals who participate in sports such as football, hockey, baseball, lacrosse, wrestling, basketball, field hockey, motocross, martial arts and boxing use mouthguards to protect their teeth, tongue, jaw, lips, and brain from injury due to impact with other players, a ball, a puck, goal posts, the ground, and any number of possible objects with which the player's face or head may forcefully sustain an impact. In several sports, the participants wear helmets of varying designs, and players attach the mouthguards to these helmets using a rubberized strap or tether. The strap attaches to one end to the mouthguard and on the other end attaches to the face guard on the helmet or some other item on the helmet that allows attachment.

A shortcoming of the current way these mouthguards attach with a tether is that while engaged in the sport, another player may grab the tether, causing pain or discomfort when the mouthguard is pulled forcefully from the mouth of the player wearing it.

A second shortcoming is the lack of sanitation that occurs because the player must use his or her hand to remove and replace the mouthguard. When removed, the player often holds the mouthguard in his or her hand, which may have dirt, sweat, blood, sputum, chemicals, animal feces, or other unsanitary debris or fluid. When replaced in the player's mouth, these unsanitary materials may enter the player's mouth. In addition, the player should be able to hold the mouthguard in such a way that the player can sanitize it by spraying a sanitizing fluid over it.

The inventor has determined that there is a need for a sports mouthguard with a tether or strap that is different from those currently available. In particular, there is a need for a mouthguard with a tether that allows the player to easily insert and remove the mouthguard from a player's mouth without touching the mouthguard and introducing unsanitary debris or fluid into the individual's mouth. There is also a need for mouthguard with a tether that attaches the mouthguard to a helmet in such a way that the mouthguard may not be pulled forcefully from an individual player's mouth. The inventor has determined from research that for optimal use of a mouthguard with a tether, these features provide advantages for the user.

SUMMARY

In one general aspect a mouthguard with a tether includes a mouthguard with an attached, extending short tether "tail" that contains a magnet at the end of the tether, a second tether portion that has an attachment means for attaching to the helmet on one end and a magnet on the other end. The end of the tether tail on the mouthguard magnetically attaches to the end of the tether portion that attaches to the helmet.

Embodiments of the mouthguard with tether may include a handle in the middle of the tether that the player may use to remove or insert the tether without touching the mouthguard. The tether also attaches to the helmet with a small hook made of a flexible material such as hard rubber or plastic.

In another implementation, the mouth guard system includes a mouth guard portion and a tether portion. The mouth guard portion is configured to be placed around a portion of a wearer's teeth and having an elongated member extending from the mouth guard portion, the elongated member including a magnet. The tether portion has a first end and a second end, the first end including a magnetic configured to mate with the magnet in the elongated member. Embodiments of the mouth guard system includes one or more of the following features. For example, the second end of the tether portion may include an attachment means for attaching the mouth guard system to an article worn by the wearer of the mouth guard. The mouth guard system may further include a sanitizing fluid to clean the mouth guard portion.

In another embodiment, there is a method of cleansing or sanitizing an object to be placed in the mouth. The method includes spraying a solution of chlorhexidine gluconate on the object in an amount sufficient to cleanse or sanitize the object. The solution includes an aqueous carrier and chlorhexidine gluconate present at a concentration in the solution of about 0.02% to about 1.2%.

Embodiments of the method may include one or more of the features described below or herein. For example, the method may include spraying a solution in which the chlorhexidine gluconate is present at a concentration in the solution of about 0.06% to about 1.0%, of about 0.09% to about 0.8%, of about 0.06% to about 0.6%, of about 0.06%, of about 0.09%, of about 0.12%, or of about 1.2%.

The solution applied may further include a flavor and glycerin. The solution may be sugar-free.

The solution applied may consists essentially of chlorhexidine gluconate to cleanse or sanitize, an aqueous carrier, glycerin and a flavor.

The method may include spraying the solution onto a mouth guard. The solution may be sprayed onto the mouth guard to remove one or more of blood, dirt, sweat, sputum, chemicals, animal feces, DNA, and saliva.

The method may include spraying the solution onto one or more of tooth brushes, eating utensils, baby pacifiers, baby bottles/nipples, sippy cups, dental retainers, and mouth pieces for musical instruments, essentially any item(s) to be placed into or onto the mouth.

The method may include applying a solution that causes a 2 log reduction in organisms for a 0.06% solution, a 2+log reduction in organisms for a 0.09% solution and/or a 4+log reduction in organisms for a 1.2% solution.

In another general aspect there is provided a method of cleansing or sanitizing a mouth guard placed in the mouth during athletic activities. The method includes spraying a solution of chlorhexidine gluconate on the mouth guard in an amount sufficient to cleanse or sanitize the mouth guard. The solution includes an aqueous carrier and chlorhexidine gluconate present at a concentration in the solution of about 0.02% to about 1.2%.

Embodiments of the method of cleansing or sanitizing a mouth guard may include one or more of the following features or those described above. For example, the chlorhexidine gluconate may be present in the solution at an amount of about 0.06% to about 0.12%.

DESCRIPTION OF THE DRAWINGS

FIG. 3 is a perspective view of a neck lanyard having one or more magnetic attachment means and a mouthguard attached.

FIG. 4 is a plan view of a mouth guard with lanyard and sanitizing solution squeeze bottle.

DETAILED DESCRIPTION

The inventor recognized that although many mouthguards with tethers exist, the majority of them are not designed to release when another player pulls on the tether. Nor do any mouthguards with tethers exist that enable the player to remove and reinsert the mouthguard without touching the mouthguard with their hands.

A mouthguard is needed that has a tether that easily pulls apart when another player grabs the tether. A mouthguard is also needed that allows the player to easily remove and insert the mouthguard without touching the guard to avoid contaminating the player's mouth with unsanitary debris and fluids.

The present mouthguard with tether described herein addresses the issue of mouthguards with tethers not releasing when another individual grabs the mouthguard tether. The present invention also addresses the issue of players contaminating mouthguards with unsanitary debris and fluids when they remove or insert mouthguards with their hands. The present invention protects the wearer's mouth when the tether is grabbed by breaking apart, leaving the mouthguard still in the player's mouth. The present invention also allows a player to sanitarily remove the mouthguard from his or her mouth and reinsert it into the mouth by grabbing a short portion of the tether rather than by grabbing the mouthguard itself. A second embodiment of the invention similarly enables a player to sanitarily remove the mouthguard from the player's mouth or reinsert it in the player's mouth by providing an integrated handle on the tether that the player can grasp.

Thus, in one general aspect, the mouthguard with tether has a standard mouthguard with a tether with a magnet inserted or embedded in the end of the tether along with a second tether portion that attaches by some connecting means to the helmet by some means. The second embodiment of the present invention has a standard mouthguard with a tether that has an integrated handle near the mouthguard, and a hook on the other end of the tether that may be hooked onto the facemask of a helmet or directly to the helmet. The mouthguard is a standard mouthguard made of thermoplastic, or other standard material for mouthguards. The tether is likely made of some plastic or other flexible, semi-durable and non-absorbent material.

Figure 1:
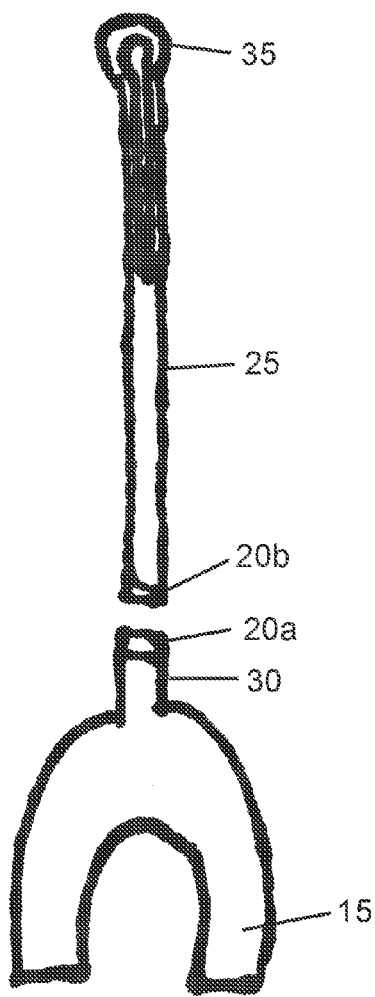
FIG. 1 is a top view of a mouth guard with magnetic attachment means.

The mouthguard with tether 10 is best seen in FIG. 1. In this embodiment of the present invention, a mouthguard 15 with a short tether portion 30 attaches to a second portion of the tether 25 by a magnetic connection 20. The magnetic connection is formed by a magnet 20a embedded or inserted in the second portion of the tether 25 connecting to a magnet 20b embedded or inserted in the short tether portion 30. The second portion of the tether 25 attaches to the facemask of a helmet or directly to the helmet by some attachment means at the end 35 of the second portion of the tether 25.

A player would use the mouthguard with tether 10 by attaching it to the facemask of a helmet or directly to the helmet using the attachment means at the end 35 of the second portion of the helmet. The player would then pick up the mouthguard 15 by the short tether portion 30 and insert it in to his or her mouth. The player would grasp the magnetic portions 20a and 20b of the second portion and short portion of the tether and bring them together to form a magnetic connection. While playing sports, if another player grabs the tether along the short portion 30 or second portion 25, as sports participants often do during competition or practice, the tether releases at the magnetic connection 20.

A secondary benefit of the present invention 10 is that when the player removes the mouthguard at any time, the player does so by grasping the short tether portion 30 and removing the mouthguard 15 without touching the mouthguard 15 with his or her hands. By grasping the short tether portion 30 as opposed to the mouthguard 15, the player does not contaminate the mouthguard with any fluids or debris that may be on the player's hands. In addition, the player may squirt or pour a sanitizing fluid onto the mouthguard 15 by holding the short tether portion 30. The player may then reinsert the mouthguard 15 without contaminating the mouthguard 15 by holding the short tether portion 30 and replacing the mouthguard 15 into his or her mouth.

Figure 2:
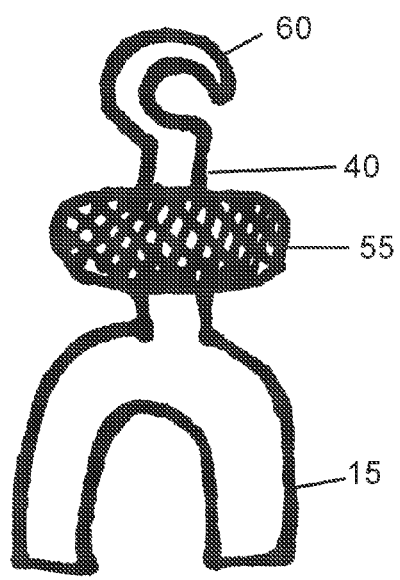
FIG. 2 is a top view of the second embodiment of the mouth guard with built-in handle.

A second embodiment 50 of the present invention is best seen in FIG. 2. In this embodiment 50, the mouthguard 15 has a tether 40 with an integrated handle 55. The tether additionally has an attachment means 60 such as a hook that attaches to the facemask of a sports helmet or attaches directly to a helmet.

This second embodiment of the mouthguard with tether 50 is used in a similar manner as the first embodiment; that is, the player would attach the mouthguard with tether 50 to a faceguard or helmet using attachment means 60 and insert the mouthguard 15 into the mouth by grasping the integrated handle 55 and placing the mouthguard 15 into the mouth. The player would remove the mouthguard 15 by grasping the integrated handle 55 and removing from his or her mouth. The mouthguard 15 would be prevented from being contaminated by additional fluids or debris because it would hang from the faceguard or helmet by the attachment means 60.

Referring to FIG. 3, in a related invention, a neck lanyard 75 includes a main portion 83, a releasable portion 79, and one or more connecting means to allow a mouthguard to be releasably attached to the lanyard or the releasable portion to be removed in part or in whole from the main portion. The releasable portion 125 is connected to the main portion 130 at two ends by one or two pairs of connecting means, 85a, 85b and 77a, 77b. The connecting means may be magnets, ball-in-socket, Velcro (hooks and loops), or other releasable means that allows the ends to be attached and released. A mouthguard 15 is connected to the neck lanyard main portion 83 using a pair of connecting means 87. As noted above, the connecting means 87 may be a pair of magnets that exert a magnetic force to stay together. The releasable portion of the mouthguard 15 may be retained in the lanyard by two pairs of connecting means 20a, 20b. Although the lanyard 75 is shown as having two pairs of connecting means that allows the releasable portion to be completely removed from the lanyard, the lanyard may be configured with only a single pair of connecting means such that the lanyard will open up upon exertion of force against the connecting means.

The lanyard 75 may be formed from a variety of materials, such as plastic, a cloth or fabric made from a natural or synthetic material, or other material that can be worn around a person's neck. The connecting means can be within the lanyard, mounted to an outer surface of the lanyard, to an end of the lanyard or otherwise attached to the lanyard such that the connecting means do not interfere with comfortable wearing of the lanyard.

In use, the lanyard 75 is worn around the neck of an athlete to allow the athlete to retain the mouth guard 15 so that it can be easily inserted into and removed from the athlete's mouth. The connecting means 20a, 20b are configured to allow the mouthguard to be easily removed from the lanyard, for example to use a different mouthguard or to be sold separately from the mouthguard. In some embodiments, the connecting means 20a, 20b are optional. The connecting means 77a, 77b and 85a, 85b are configured to permit their separation from each other if the lanyard is placed in tension, for example during an athletic event. Such tension is placed on the lanyard if an opponent grabs the lanyard. In such even, the lanyard will open up such that the athlete wearing the lanyard will not be injured.

Referring to FIG. 4, in another embodiment, the mouth guards described herein may be used with a sanitizing solution in a squeeze bottle or other container such that the athlete can periodically clean and/or sanitize the mouth guard during an athletic event. An athlete may need to use the sanitizer squeeze bottle and sanitizer solution during an athletic event if the mouth guard falls on the ground or otherwise is contaminated during the event. The mouth guard 15, squeeze bottle with sanitizing solution 93 and lanyard 75 may be provided in a kit form 90 that an athlete can purchase. The kit 90 can include the mouth guard 15 and lanyard 75 only or optionally with the squeeze bottle 93. Similarly, the kit 90 can include the mouth guard 15 and squeeze bottle only with a sanitizing solution 93 and optionally include the lanyard 75.

The sanitizing solution can be providing as a separate item or along with a squeeze bottle or other dispensing container for using the solution during a sporting event. The solution can include an antibacterial agent selected to be effective against the bacteria that is likely to be found on a piece of sporting equipment, such as a mouth guard. One such antibacterial agent is chlorhexidine.

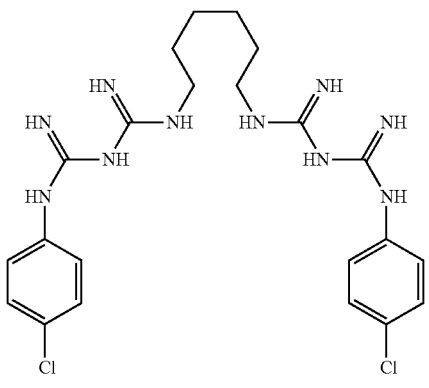

Chlorhexidine

Chlorhexidine is a chemical antiseptic that is effective on both Gram-positive and Gram-negative microbes, although it is reported to be less effective with some Gram-negative microbes. It is also useful against fungi and enveloped viruses. It has bactericidal and bacteriostatic mechanisms of action. The mechanism of action is membrane disruption. Currently, chlorhexidine is used in some contact lens solutions, oral rinses and skin cleansers, and as a preservative. Chlorhexidine is also used as in mouthwashes designed to reduce dental plaque and oral bacteria and therefore can be used to improve bad breath. In oral applications, it has been shown to have an immediate bactericidal action and a prolonged bacteriostatic action due to adsorption onto the pellicle-coated enamel surface. Chlorhexidine is available in the gluconate salt form as chlorhexidine gluconate, however, chlorhexidine can be used in other salt forms.

The inventor has determined that chlorhexidine gluconate also can be used to treat items that are placed in the mouth without using the chlorhexidine in the mouth, for example, as an antibacterial agent for mouthguards used in sports. Other items that can be cleaned or sanitized with the solution include tooth brushes, eating utensils, baby pacifiers, baby bottles/nipples, sippy cups, dental retainers, mouth pieces for musical instruments, essentially anything to be placed into, or onto the mouth, etc. In general, the composition can be applied to any article that is placed in the mouth or is likely to be placed in the mouth.

Such liquid solutions for treating a mouth guard or other article have the following compositions:

| Example 1 - 1.2% Chlorhexidine Gluconate Solution | | |
|---|---|---|
| Item | Ingredients | Quantity (g) |
| 1 | Water | 469.56 |
| 2 | Chlorhexidine Gluconate* | 30.000 |
| 3 | Glycerine | 0.4001 |
| 4 | Mint Flavor | 0.0344 |
| | Total | 500.0 |

| Example 2 - 0.09% Chlorhexidine Gluconate Solution | | |
|---|---|---|
| Item | Ingredients | Quantity (g) |
| 1 | Water | 497.514 |
| 2 | Chlorhexidine Gluconate* | 2.2353 |
| 3 | Glycerine | 0.2338 |
| 4 | Mint Flavor | 0.0172 |
| | Total | 500.0 |

| Example 3 - 0.06% Chlorhexidine Gluconate Solution | | |
|---|---|---|
| Item | Ingredients | Quantity (g) |
| 1 | Water | 498.265 |
| 2 | Chlorhexidine Gluconate* | 1.5060 |
| 3 | Glycerine | 0.2013 |
| 4 | Mint Flavor | 0.0280 |
| | Total | 500.0 |

The formulations include water as a carrier, chlorhexidine gluconate as an ant-bacterial agent, glycerine as a sweetener and humectant, and mint to flavor the composition. The sweetener can be substituted with one or more of xylitol (1 to 8%), sucrose (0.5 to 8%), maltose (0.5 to 8%), etc. The use of glycerine or glycerol as a humectant may be replaced by another ingredient, such as propylene glycol, polyethylene glycol (PEG) or hydroxypropyl methylcellulose (HPMC).

Other flavors can be used instead of mint. Such flavors can be natural or artificial. Color can be used as additive to identify different strengths or flavors. For example, for mint flavor the color green can be used in the formulation to identify the composition as mint as well as to give the impression of a mint flavor. The formulation can be sugar free and use xylitol for sweetening. The formulation can consist essentially of the chlorhexidine gluconate to cleanse or sanitize with the other excipients functioning as carriers, preservatives, sweeteners, taste masking, etc. The formulation can consist essentially of chlorhexidine gluconate to cleanse or sanitize an object, a sweetener, a flavor and an aqueous carrier. The formulation also can consist of the ingredients described above.

The percent range of chlorhexidine gluconate for this product can be about 0.02 to about 1.2% chlorhexidine gluconate, from about 0.04 to about 1.1% chlorhexidine gluconate, from about 0.06 to 1.0% chlorhexidine gluconate, from about 0.08 to 0.90% chlorhexidine gluconate, from about 0.1 to about 0.8% chlorhexidine gluconate, from about 0.2 to about 0.6% chlorhexidine gluconate, and about 0.4% chlorhexidine gluconate. Values within this range also are acceptable. Further, a value for the percentage of chlorhexidine gluconate in the composition should be interpreted broadly enough to encompass typical overages used in the pharmaceutical industry. Chlorhexidine gluconate is typically provided in a dilute solution of 20% chlorhexidine gluconate.

The above formulations are made as follows:
1. Weigh all ingredients according to the formula.
2. Add Chlorhexidine gluconate to the water and mix using lighting mixer for 10 minutes.
3. Add item the glycerine slowly while the lighting mixer for 5 minutes of the solution of step #2.
4. Add item the flavor (e.g., mint) slowly into the solution of step #3 and mix for 5 minutes using lighting mixer.

It should be understood that the formulations described above can be varied in the range described herein (e.g., 0.02% to 1.2%) by merely varying the amount of water, glycerin and flavor to accommodate the specified percentage of chlorhexidine gluconate. Such modifications are well within one of ordinary skill in the art.

During the development work, it was noted that adding more than 0.5% glycerin creates turbidity and reduces miscibility between the flavor and the chlorhexidine gluconate. Adding more than 0.1% of flavor also tends to form a complexation between the glycerin and the flavor, creating a separate layer over the water phase upon standing. For these reasons, it was recommended to use less than 0.5% glycerin and less than 0.1% flavor.

A stability study was conducted using the 0.6, 0.9 and 1.2% solutions. The stability study was conducted under 40° C./75% RH conditions. All three solutions were kept for two weeks. At time zero, one week and two weeks an observation was made for any settling, cloudy or any unusual particles in the solution. During this two week study none of these conditions were observed.

The formulations described above have been tested in conditions intended to replicate the use of the sanitizing mouthwash to clean a mouthguard. In the testing process, the organism, *Candida albicans*, is applied to a mouthguard and the counts of the organism measured on the surface. Then the amount of the organism is measured on the mouthguard. Next the mouthwash is rinsed with the sanitizing solution. The table below provides the bacteria counts measured for each of these steps.

Each culture strain was grown in Tryptic Soy Agar With Yeast Extract (TSAYE) from standing overnight cultures incubated at 35+/−2° C. Standing overnight cultures were grown over three passages. This standing overnight culture was expected to contain between 10×8 to 10×9 cfu/milliliter. 0.1 ml of each 10×9 organism broth culture was transferred to a sterile dilution tube containing 9.9 ml of sterile butterfield's buffer. This results in a 10×7 organism dilution.

For the mouthguard inoculation, 0.01 ml of the 10×7 organisms dilution is then applied to the mouthguard and the mouth guard is allowed to stabilize over a period of one hour in an incubation held at 30° C. This would approximate a mouth guard inoculated with 100,000 organisms or colony forming units (CFU).

To analyze the sample, one inoculated mouthguard was rinsed with 15 ml of each concentrated chlorhexidine gluconate solution and allowed to dry. One inoculated mouthguard was not rinsed and was set aside. Mouthguards were aseptically placed in individual glass jars containing 100 ml of sterile Butterfields buffer. The jars were shaken for one minute by hand. The liquid suspension was then vacuum-filtered through the filtration apparatus. The filter was then removed and placed face-up onto a pre-poured DE AGAR plate. Plates were incubated for at 35° C. for 48 hours. The counts were recorded and compared to controls for enumeration.

| | Initial Inoculum Level | | |
|---|---|---|---|
| Organism | 0.06% chlorhexidine | 0.09% chlorhexidine | 1.2% chlorhexidine |
| *Escherichia coli.* | 6,200,000 | 6,200,000 | 100,000 |
| *Streptococcus* | 2400 | 2400 | N/A |
| *Salmonella* | 11,160,000 | 11,160,000 | 180,000 |
| *Candida albicans* | 372,000 | 372,000 | 144,000 |
| *Staphylococcus* | 7,440,000 | 7,440,000 | 220,000 |

| | Mouthguard (without rinse) | | |
|---|---|---|---|
| Organism | 0.06% chlorhexidine | 0.09% chlorhexidine | 1.2% chlorhexidine |
| *Escherichia coli.* | 49,600 | 49,600 | 120,000 |
| *Streptococcus* | 200 | 200 | N/A |
| *Salmonella* | 250,000 | 250,000 | 9,000 |
| *Candida albicans* | 100 | 100 | 16,000 |
| *Staphylococcus* | 248,000 | 248,000 | 24,000 |

| | Mouthguard (with sanitizing rinse) | | |
|---|---|---|---|
| Organism | 0.06% chlorhexidine | 0.09% chlorhexidine | 1.2% chlorhexidine |
| *Escherichia coli* | 2,500 | 248 | <1 |
| *Streptococcus* | <1 | <1 | N/A |
| *Salmonella* | 2,500 | 1736 | <1 |
| *Candida albicans* | 1 | <1 | 2 |
| *Staphylococcus* | 2,500 | 2,480 | <1 |

An additional test was run on the mouthguard that had been inoculated with Candida albicans and measured to have a level of 16,000 counts. The mouthguard was rinsed with water and found to have a level of 1,500 counts.

Overall, the experiment demonstrated a 2 log reduction for the 0.06% solution, a 2+log reduction for the 0.09% solution and a 4+log reduction for the 1.2% solution. Each of these reductions is a desirable amount and shows the efficacy of the solution for treating a mouth guard by eliminating the organisms that are likely to be found on such an object during typical use.

In use for cleaning or sanitizing a mouth guard, an athlete will remove the guard from his mouth and apply, spray or rinse the mouth guard with the solution. The athlete will apply an amount sufficient to give the perception that the mouth guard has been cleaned. The amount applied can vary based on the user's preference. For example, an amount of 10 ml, 20 ml, 30 ml, 40 ml, 50 ml, etc. up to 100 ml (in 10 ml increments) can be applied to the mouth guard to cleanse and/or sanitize the mouth guard. The mouth guard also can be dipped into a solution of the chlorhexidine gluconate if desired.

In another embodiment, the chlorhexidine gluconate solution can be provided on a wipe form similar to alcohols wipes. The chlorhexidine gluconate wipes can be individually packaged and used to clean or sanitize surfaces, for example, of utensils at restaurants or other objects that are inserted into the mouth. The chlorhexidine gluconate can be present on the wipes in any of the concentrations disclosed herein.

While several particular forms of the invention have been illustrated and described, it will be apparent that various modifications and combinations of the invention detailed in the text and drawings can be made without departing from the spirit and scope of the invention. For example, the present invention might combine features of both the first embodiment and second embodiment, resulting in a mouthguard with in integrated handle that easily releases from a magnetic connecting means along the tether. In addition, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

What is claimed is:

1. A method of cleansing or sanitizing a dental retainer or a mouth guard to be placed in the mouth, the method comprising spraying a solution of chlorhexidine gluconate on the object in an amount sufficient to cleanse or sanitize the object, wherein the solution consists of chlorhexidine gluconate to cleanse or sanitize, water, glycerin and a flavor, wherein the chlorhexidine gluconate is present at a concentration in the solution of about 0.02% to about 1.2%.

2. The method of claim 1, wherein the method comprises spraying a solution in which the chlorhexidine gluconate is present at a concentration in the solution of about 0.06% to about 1.0%.

3. The method of claim 1, wherein the method comprises spraying a solution in which the chlorhexidine gluconate is present at a concentration in the solution of about 0.09% to about 0.8%.

4. The method of claim 1, wherein the method comprises spraying a solution in which the chlorhexidine gluconate is present at a concentration in the solution of about 0.06% to about 0.6%.

5. The method of claim 1, wherein the method comprises spraying a solution in which the chlorhexidine gluconate is present at a concentration in the solution of about 0.06%.

6. The method of claim 1, wherein the method comprises spraying a solution in which the chlorhexidine gluconate is present at a concentration in the solution of about 0.09%.

7. The method of claim 1, wherein the method comprises spraying a solution in which the chlorhexidine gluconate is present at a concentration in the solution of about 0.12%.

8. The method of claim 1, wherein the method comprises spraying a solution in which the chlorhexidine gluconate is present at a concentration in the solution of about 1.2%.

9. The method of claim 1, wherein the solution is sprayed onto the mouth guard to remove one or more of blood, dirt, sweat and saliva.

10. The method of claim 1, wherein the solution applied causes a 2 log reduction in organisms for a 0.06% solution, a 2+log reduction in organisms for a 0.09% solution and a 4+log reduction in organisms for a 1.2% solution.

11. The method of claim 1, wherein the solution is sugar-free.

12. A method of cleansing or sanitizing a mouth guard placed in the mouth during athletic activities, the method comprising spraying a solution of chlorhexidine gluconate on the mouth guard in an amount sufficient to cleanse or sanitize the mouth guard, wherein the solution consists of chlorhexidine gluconate to cleanse or sanitize, water, glycerin and a flavor, wherein the chlorhexidine gluconate is present at a concentration in the solution of about 0.02% to about 1.2%.

13. The method of claim 12, wherein the chlorhexidine gluconate is present in the solution at an amount of about 0.06% to about 0.12%.

14. The method of claim 12, wherein the solution is sprayed onto the mouth guard to remove one or more of blood, dirt, sweat and saliva.

15. The method of claim 12, wherein the solution applied causes a 2 log reduction in organisms for a 0.06% solution, a 2+log reduction in organisms for a 0.09% solution and a 4+log reduction in organisms for a 1.2% solution.

16. The method of claim 12, wherein the solution is sugar-free.

* * * * *